(12) United States Patent
Hung

(10) Patent No.: US 9,463,111 B2
(45) Date of Patent: Oct. 11, 2016

(54) PORTABLE URINATING DEVICE

(71) Applicant: Chung-Pin Hung, New Taipei (TW)

(72) Inventor: Chung-Pin Hung, New Taipei (TW)

( * ) Notice: Subject to any disclaimer, the term of this patent is extended or adjusted under 35 U.S.C. 154(b) by 157 days.

(21) Appl. No.: 14/468,366

(22) Filed: Aug. 26, 2014

(65) Prior Publication Data

US 2015/0059071 A1 Mar. 5, 2015

(30) Foreign Application Priority Data

Aug. 28, 2013 (TW) .............................. 102130942 A

(51) Int. Cl.
*A47K 11/00* (2006.01)
*A61F 5/453* (2006.01)
*A61F 5/455* (2006.01)

(52) U.S. Cl.
CPC ............. *A61F 5/453* (2013.01); *A61F 5/4556* (2013.01); *A47K 11/00* (2013.01)

(58) Field of Classification Search
CPC ...................................................... A61G 9/006
USPC ................................................ 4/144.1–144.3
See application file for complete search history.

(56) References Cited

U.S. PATENT DOCUMENTS

| | | | | |
|---|---|---|---|---|
| 4,241,017 A * | 12/1980 | Balistreri | ............... | A61B 5/208 4/144.1 |
| 5,406,650 A * | 4/1995 | Einbinder | ............... | A47K 11/12 383/100 |
| 5,956,782 A * | 9/1999 | Olguin | ................... | A47K 11/12 4/144.1 |
| 6,129,892 A * | 10/2000 | Garrett | ...................... | A61L 9/01 422/1 |
| 6,212,691 B1 * | 4/2001 | Heberer | ................. | A47K 11/12 4/144.1 |
| 6,425,411 B1 * | 7/2002 | Gorges | ...................... | E03C 1/28 137/247.39 |
| 6,546,566 B1 * | 4/2003 | Geisel | .................... | A47K 11/12 4/144.1 |
| 6,684,414 B1 * | 2/2004 | Rehrig | ................... | A47K 11/12 4/144.1 |
| 6,732,384 B2 * | 5/2004 | Scott | ....................... | A47K 11/12 4/144.1 |
| 6,912,737 B2 * | 7/2005 | Ernest | .................... | A47K 11/12 4/144.1 |
| 6,968,577 B1 * | 11/2005 | Taft, Jr. | .................. | A47K 11/12 4/144.1 |
| 7,363,661 B1 * | 4/2008 | Myers | .................... | A47K 11/12 4/144.1 |
| 8,650,669 B1 * | 2/2014 | Kolter | .................... | A47K 11/12 4/144.1 |
| 8,690,846 B2 * | 4/2014 | Chen | ....................... | A61F 5/451 4/144.1 |
| 2010/0199412 A1 * | 8/2010 | McAlpine | ............. | E03D 13/005 4/144.1 |
| 2014/0033414 A1 * | 2/2014 | Kolter | .................... | A47K 11/12 4/144.3 |
| 2015/0305917 A1 * | 10/2015 | Su | ........................... | A61F 5/451 4/144.1 |

* cited by examiner

*Primary Examiner* — Lori Baker

(57) ABSTRACT

A portable urinating device includes a cover portion, a contact portion and a main body. The cover portion includes a cover with holes covering a holding portion. The contact portion is located on the opening of the main body, and the contact portion has a curve opening to meet the outer shape of urinary organ of human and the main body can be used to contain urine.

13 Claims, 5 Drawing Sheets

PORTABLE URINATING DEVICE

BACKGROUND OF THE INVENTION

1. Field of the Invention

The present invention relates to a portable urinating device, and especially a potable urinating device.

2. Description of the Related Art

When people go outside and want to urinate, we sometimes hardly find a restroom. Therefore, men might use beverage bottles to contain the urine. However, the opening of the beverage bottle might not be suitable for men. So some men just urinate outside but which does not look good, might smell and pollute the environment.

On the other hand, there are disposable urinating device for women. But the device is used for women standing to urinate, which is also no help for the situation that people cannot find a restroom when going outside.

SUMMARY OF THE INVENTION

A primary object of the present invention is to provide a reusable portable urinating device. Another object is to provide is to provide a portable urinating device that a user can use anytime and anywhere.

To achieve the abovementioned object, the present invention provides a portable urinating device comprising a cover portion, a contact portion and a main body. The cover portion comprises a holding portion and a cover with holes, and the cover with holes convers the holding portion. The contact portion comprises a nonplanar curve opening, and the contact portion 20 is located at the opening of the main body. The main body and the cover portion can be integrated to make the contact portion be located between the main body and the cover portion. When using the portable urinating device, a user can open the cover portion and separate it from the main body, and then use the contact portion located on the main body to meet the outer shape of urinary organ and store the urine temporarily. After the urine is poured out in an appropriate place, the device can be cleaned and used again.

In a better embodiment, the main body comprises an inner trough and an outer case wrapping the inner trough and they are mutually partially fastened together; further, the outer case and the inner trough respectively comprises a recess and a corresponding tenon, whereby the outer case and the inner trough are mutually fastened via the recess and the corresponding tenon. The lower perimeter of the contact portion is fastened between the outer case and the inner trough.

In an embodiment, the cover portion further comprises a base. The holding portion and the base respectively comprise a groove and a corresponding hook, and the holding portion and the base are mutually fastened via the groove and the corresponding hook. Moreover, the holding portion and the base respectively comprise a hole and a corresponding pin, and the holding portion and the base are mutually fastened via the hole and the corresponding pin. The cover portion is located below the interior of the holding portion, and when the main body is combined with the cover portion, the upper perimeter of the contact portion is located between the base and the holding portion.

In addition, the cover portion further comprises an O-ring and the base comprises a holding groove, and the O-ring is located in the holding groove, whereby the filled urine can be blocked in the main body when the main body and the cover portion are combined.

BRIEF DESCRIPTION OF THE DRAWINGS

These and other objects and advantages of the present invention will become apparent from the following description of the accompanying drawings, which disclose several embodiments of the present invention. It is to be understood that the drawings are to be used for purposes of illustration only, and not as a definition of the invention.

In the drawings, wherein similar reference numerals denote similar elements throughout the several views.

DETAILED DESCRIPTION OF THE PREFERRED EMBODIMENT

To clarify the above and other purposes, features, and advantages of this invention, a specific embodiment of this invention is especially listed and described in detail with the attached figures as follows.

Figure 1:
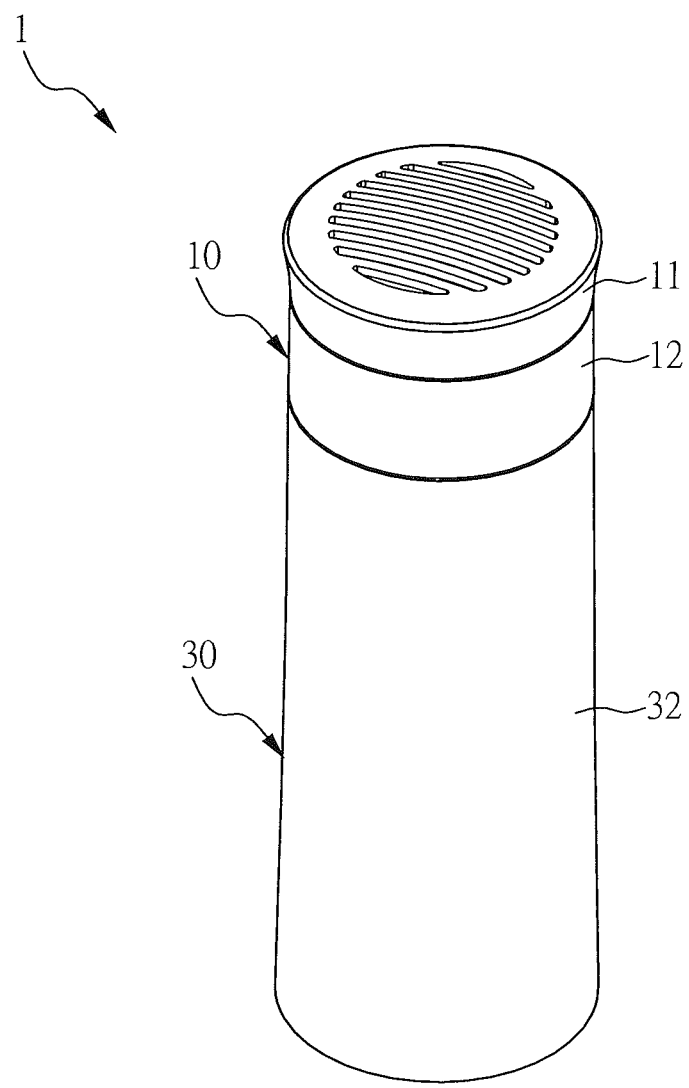
FIG. 1 illustrates a perspective view of a portable urinating device.
Figure 2:
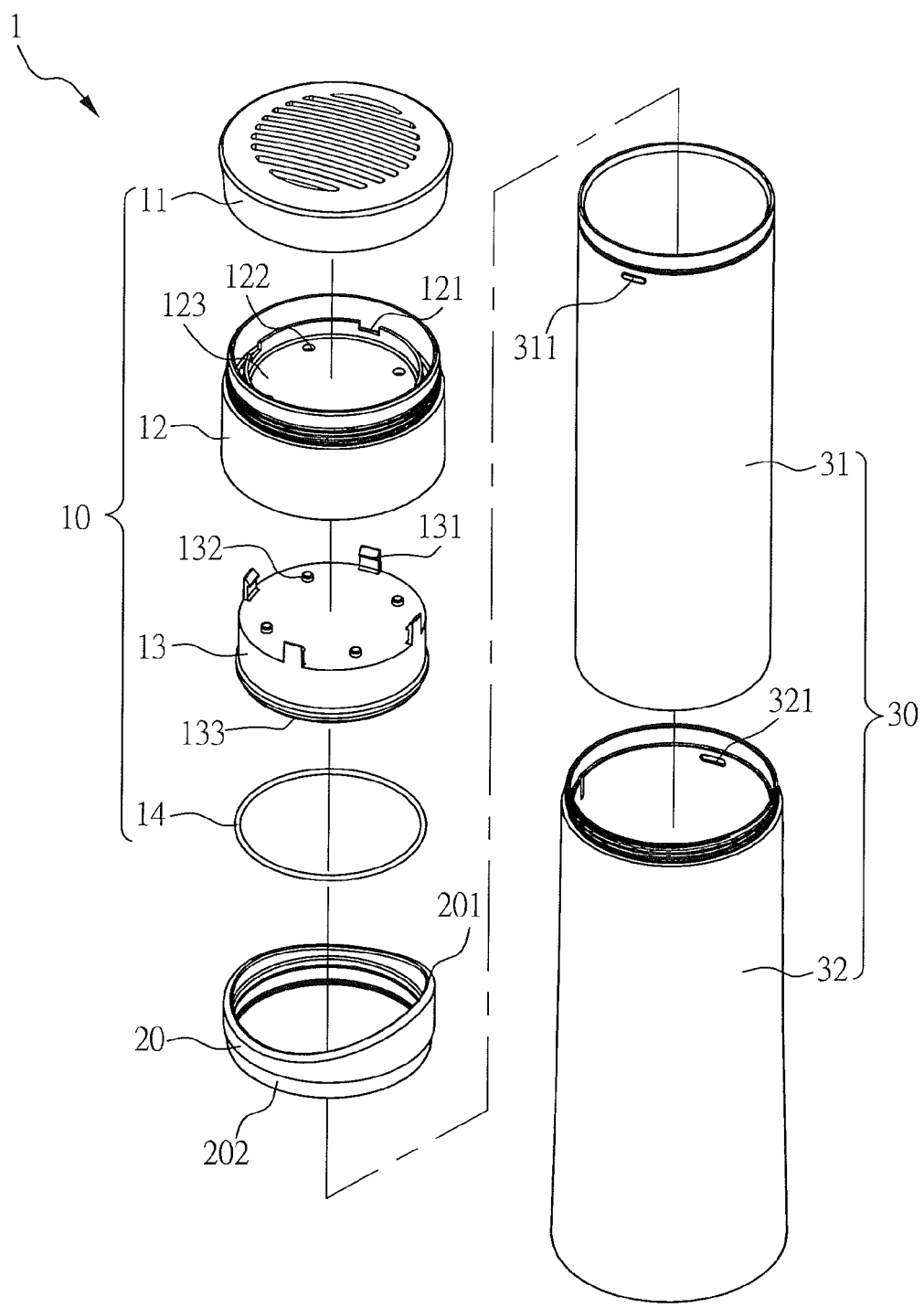
FIG. 2 illustrates an exploded perspective view of a portable urinating device according to FIG. 1.

Please refer to FIG. 1 and FIG. 2, which are schematic drawings of a portable urinating device. The present invention provides a portable urinating device 1 comprising a cover portion 10, a contact portion 20 and a main body 30.

Figure 3:
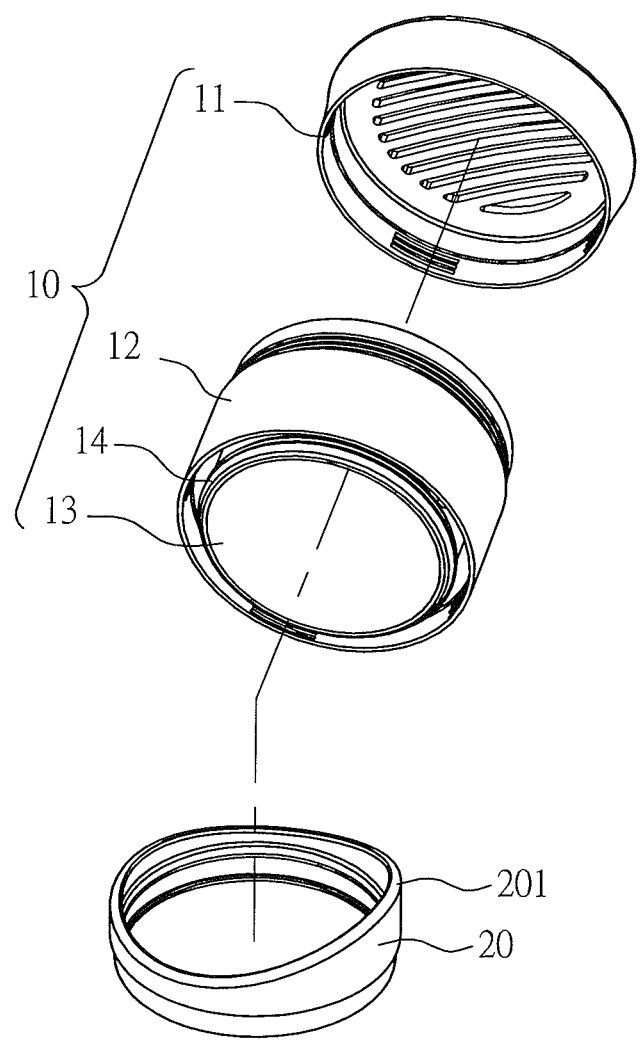
FIG. 3 illustrates a partially exploded perspective view of the portion between the cover portion and the contact portion.
Figure 4:
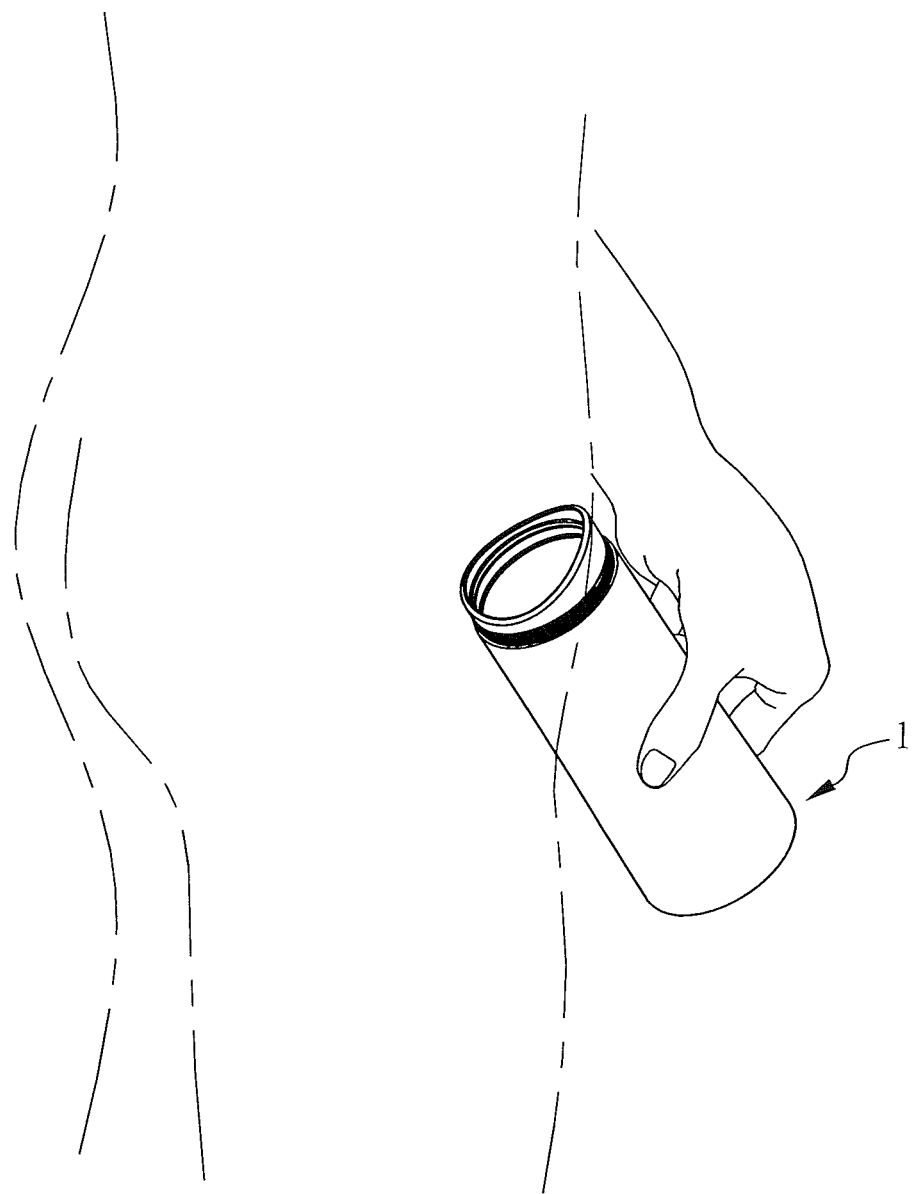
FIG. 4 illustrates a schematic drawing of use of a portable urinating device.
Figure 5:
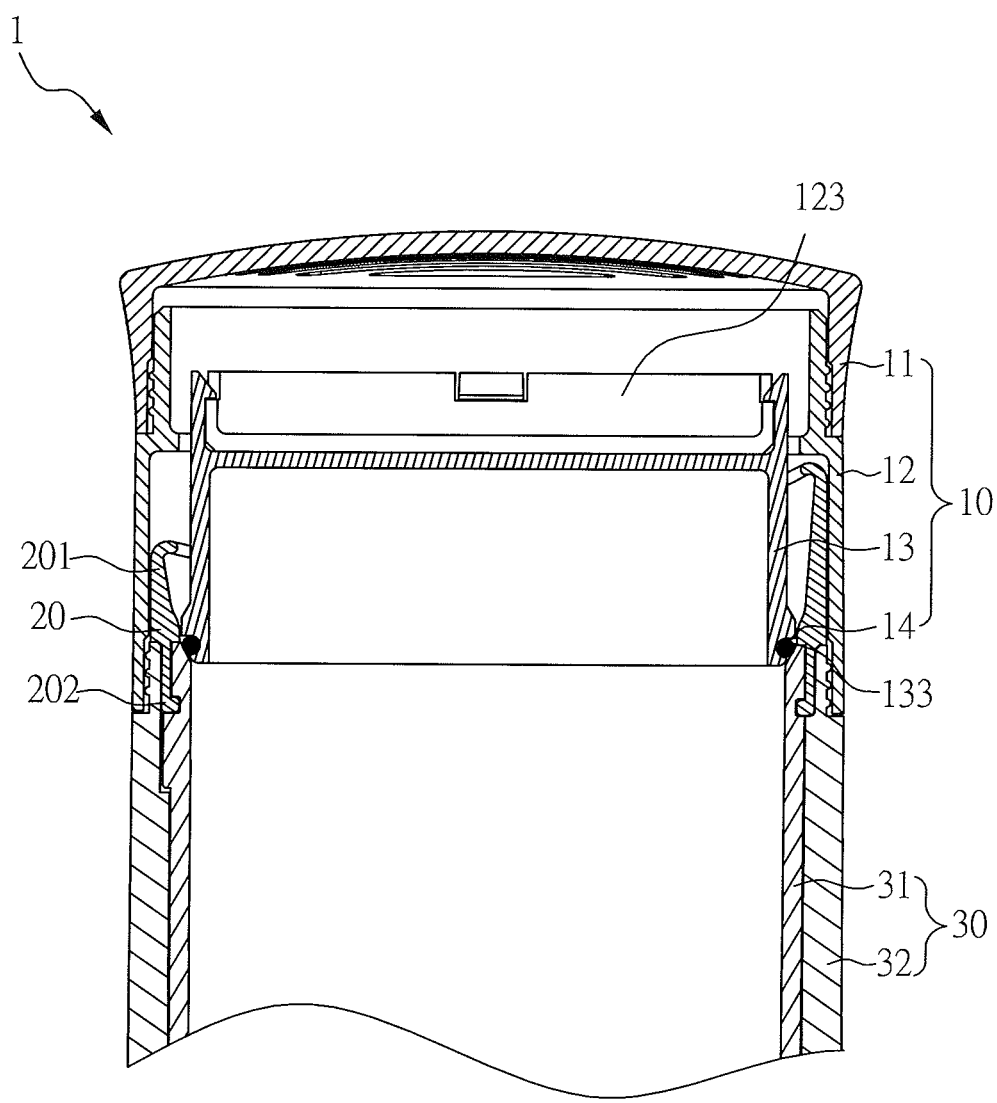
FIG. 5 illustrates a cross-sectional schematic drawing of a portable urinating device.

Please refer to FIG. 3, the contact portion 20 comprising a nonplanar curve opening 201. As shown in FIG. 2 and FIG. 4, the contact portion 20 is located on the opening of the main body 30, the main body 30 and the cover portion 10 can be integrated and the contact portion 20 is between the main body 30 and the cover portion 10 (as shown in FIG. 5).

Please refer to FIG. 4, when using the portable urinating device 1, the user can rotate the cover portion 10 to open and separate it from the main body 30. The contact portion 20 located on the main body 30 is used to meet the outer shape of urinary organ of human and the main body 30 can be used to contain urine. Although the contact portion 20 and the main body 30 are separated in the figures, they can be integral as well. So the embodiment is just for explaining and the present invention is not limited. People skilled in art understand that the contact portion 20 and the main body 30 are in combination when they are integral. In a better embodiment, the contact portion 20 can be separated from the main body 30. That is, the contact portion 20 is located in the opening of the main body 30. The material of the contact portion 20 is flexible polymer (e.g. silica gel) in this embodiment and can be different material from the main body 30. The contact portion 20 made from flexible polymer not only provides better touch but also deforms the shape itself to fit human body tightly. Therefore, the portable urinating device 1 is suitable for the male and the female. After the urine is poured out, the portable urinating device 1 can be cleaned and used again.

In a better embodiment, please refer to FIG. 2, the cover portion 10 comprises a holding portion 12 and a cover with holes 11, and the cover with holes 11 covers the holding portion 12. The holding portion 12 further comprises a holding recess 123 which can be put some perfume, essence to give off a good smell.

The main body 30 comprises an inner container 31 and an outer case 32 wrapping the inner container 31 and they are mutually partially fastened together. Furthermore, the outer case 32 and the inner container 31 respectively comprise a recess 321 and a corresponding tenon 311, whereby the outer case 32 and the inner container 31 are mutually fastened via the recess 321 and the corresponding tenon 311. The main body 30 doesn't have to include the outer case 32 and the inner container 31. As long as the main body 30 has the function to contain the urine. In another word, the outer case 32 and the inner container 31 can be merged to one container in some embodiment, and it is also enough to contain the urine.

Please refer to FIG. 2 in conjunction with FIG. 3, in an embodiment, the cover portion 10 further comprises a base 13 combined with the holding portion 12. The holding portion 12 and the base 13 respectively comprise a groove 121 and a corresponding hook 131, and the holding portion 12 and the base 13 are mutually fastened via the groove 121 and the corresponding hook 131. Furthermore, the holding portion 12 and the base 13 respectively comprise a recessed hole 122 and a corresponding pin 132, and the holding portion 12 and the base 13 are mutually fastened via the recessed hole 122 and the corresponding pin 132. After being combined, the base 13 is located below the interior of the holding portion 12.

In addition, the cover portion 10 further comprises an O-ring 14 and the base 13 comprises a holding groove 133, and the O-ring 14 is located in the holding groove 133.

Please refer to FIG. 5, the lower perimeter 202 of the contact portion 20 is fastened between the outer case 32 and the inner container 31. After the main body 30 and the cover portion 10 are combined, the upper perimeter of the contact portion 20 (curve opening 201) is located between the base 13 and the holding portion 12. The O-ring 14 is located in the holding groove 133 of the base 13 whereby the filled urine can be blocked in the main body 30

Moreover, the portable urinating device 1 can be put in a confined space (e.g. in a car) in a long time by giving off good smell from some perfume, essence in the holding recess 123 of the holding portion 12, which doesn't make people uncomfortable. Even though the urine is not contained in the device, similar things such as perfume and essence can still be used as air refresher.

It should be noted that, although exemplary embodiments of the present invention have been shown and described, the present invention is not limited to the described exemplary embodiments. Instead, it will be appreciated by those skilled in the art that changes may be made to these exemplary embodiments without departing from the principles and spirit of the invention, the scope of which is defined by the claims and their equivalents.

I claim:

1. A portable urinating device comprising:
    a cover portion comprising a holding portion and a cover with holes,
    wherein the cover with holes covers the holding portion;
    a contact portion comprising a nonplanar curve opening; and
    a main body, wherein the contact portion is located on the opening of the main body, the main body and the cover portion can be integrated and the contact portion is between the main body and the cover portion;
    whereby the cover portion can be separated from the main body before a user is going to use the portable urinating device, and the contact portion located on the main body is able to meet the outer shape of human urinary organ when the user is urinating;
    wherein the cover portion further comprises a base combined with the holding portion and located below the interior of the holding portion, and when the main body is combined with the cover portion, the upper perimeter of the contact portion is located between the base and the holding portion.

2. The portable urinating device as claimed in claim 1, wherein the contact portion and the main body are integral.

3. The portable urinating device as claimed in claim 1, wherein the holding portion and the base respectively comprise a groove and a corresponding hook, and the holding portion and the base are mutually fastened via the groove and the corresponding hook.

4. The portable urinating device as claimed in claim 3, wherein the holding portion and the base respectively comprise a recessed hole and a corresponding pin, and the holding portion and the base are mutually fastened via the recessed hole and the corresponding pin.

5. The portable urinating device as clamed in clam 1, wherein the cover portion further comprises an O-ring and the base comprises a holding groove, and the O-ring is located in the holding groove, whereby the filled urine can be blocked in the main body when the main body and the cover portion are combined.

6. The portable urinating device as claimed in claim 1, wherein the main body comprises an inner container and an outer case wrapping the inner container and they are mutually partially fastened together, and the lower perimeter of the contact portion is fastened between the outer case and the inner container.

7. The portable urinating device as claimed in claim 6, wherein the cover portion further comprises a base combined with the holding portion and located below the interior of the holding portion, and when the main body is combined with the cover portion, the upper perimeter of the contact portion is located between the base and the holding portion.

8. The portable urinating device as claimed in claim 7 wherein the holding portion and the base respectively comprise a groove and a corresponding hook, and the holding portion and the base are mutually fastened via the groove and the corresponding hook.

9. The portable urinating device as claimed in claim 8, wherein the holding portion and the base respectively comprise a recessed hole and a corresponding pin, and the holding portion and the base are mutually fastened via the recessed hole and the corresponding pin.

10. The portable urinating device as claimed in claim 7, wherein the cover portion further comprises an O-ring and the base comprises a holding groove, and the O-ring is located in the holding groove, whereby the filled urine can be blocked in the main body when the main body and the cover portion are combined.

11. The portable urinating device as claimed in claim 6, wherein the outer case and the inner container respectively comprise a recess and a corresponding tenon, whereby the outer case and the inner container are mutually fastened via the recess and the corresponding tenon.

12. The portable urinating device as claimed in claim 1, wherein the contact portion is located in the opening of the main body, and the material of the contact portion is flexible polymer.

13. The portable urinating device as claimed in claim 12, wherein the material of the contact portion is silica gel.

\* \* \* \* \*